(12) United States Patent
Applegate et al.

(10) Patent No.: US 7,325,927 B2
(45) Date of Patent: Feb. 5, 2008

(54) METHOD OF FILTERING DATA FOR THE OBJECTIVE CLASSIFICATION OF EYES

(75) Inventors: Raymond A. Applegate, Kingwood, TX (US); Jason Marsack, Houston, TX (US); Konrad Pesudovs, Genelg (AU)

(73) Assignee: The University of Houston, Houston, TX (US)

( * ) Notice: Subject to any disclaimer, the term of this patent is extended or adjusted under 35 U.S.C. 154(b) by 201 days.

(21) Appl. No.: 11/329,430

(22) Filed: Jan. 11, 2006

(65) Prior Publication Data
US 2006/0187413 A1    Aug. 24, 2006

Related U.S. Application Data
(60) Provisional application No. 60/642,903, filed on Jan. 11, 2005.

(51) Int. Cl.
*A61B 3/00* (2006.01)
(52) U.S. Cl. .................................. 351/246; 351/200
(58) Field of Classification Search ................ 359/246
See application file for complete search history.

(56) References Cited

U.S. PATENT DOCUMENTS

| | | | | |
|---|---|---|---|---|
| 2004/0088050 A1* | 5/2004 | Norrby et al. | ............. | 623/6.11 |
| 2005/0200809 A1* | 9/2005 | Dreher et al. | ............. | 351/246 |

OTHER PUBLICATIONS

Schwiegerling J, Greivenkamp JE. Keratoconus detection based on videokeratoscopic height data. Optom Vis Sci. Dec. 1996;73(12):721-8.
Smolek, MK Klyce, Brenner DS Zernike Polynomial Terms and Corneal Indexes as Neural Network Inputs for Videokeratography Classification [ARVO Abstract]. Invest Ophthalmol Vis Sci 1997;38(4):S920. Abstract nr 4298.
Gobbe M, Guillon M. Corneal wavefront aberration measurements to detect keratoconus patients. Cont Lens Anterior Eye. Jun. 2005;28(2):57-66. Epub Feb. 25, 2005.
Carvalho LA. Preliminary results of neural networks and zernike polynomials for classification of videokeratography maps. Optom Vis Sd. Feb. 2005;82(2): 151-8.
Klyce SD, Karon MD, Smolek MK. Screening patients with the corneal navigator. J Refract Surg. Sep.-Oct. 2005;21(5 Suppl):S617-22.
Twa MD, Parthasarathy S, Roberts C, Mahmoud AM, Raasch TW, Bullimore MA. Automated decision tree classification of corneal shape. Optom Vis Sci. Dec. 2005;82(12)1038-46.

* cited by examiner

*Primary Examiner*—Scott J. Sugarman
*Assistant Examiner*—DaWayne A Pinkney
(74) *Attorney, Agent, or Firm*—Jennifer S. Sickler; Gardere Wynne Sewell LLP

(57) ABSTRACT

A method for classifying a patient's eye includes the steps of:
- obtaining normal and abnormal wavefront aberration data from normal and abnormal eyes;
- fitting the normal and abnormal eye wavefront aberration data with a basis function to decompose the normal and abnormal eye wavefront aberration data into normal and abnormal eye mathematical components;
- examining the normal and abnormal eye mathematical components to develop mathematical optical filters capable of discriminating between normal and abnormal eyes, using statistical methods to define a probability distribution;
- obtaining wavefront aberration data from the patient's eye;
- fitting the patient's wavefront aberration data with a basis function to decompose the patient's wavefront aberration data into the patient's set of mathematical components;
- examining the patient's set of mathematical components using the mathematical optical filters to generate a patient filter value; and
- classifying the patient's eye by comparing the patient filter value with the probability distribution.

13 Claims, 2 Drawing Sheets

Periodic representation of a subset of modes of the Zernike expansion
displayed using double index notation.

Periodic representation of a subset of modes of the Zernike expansion displayed using double index notation.

Example Optical Detection Filters

(Zernike coefficients listed in single index notation)

7,8,11,13,17,18,23,25,31,32,39,41,49,50,59,61

7,8,11,13,17,18,23,25,31,32

7,8,11,13,17,18,23,25, 1,2,6,7,8,9,11,12,13,17,18,23,24,25,31,32,39,40,41,49,50,59,60,61

6-65

6,7,8,9,10,11,12,13,14,15,16,17,18,19,20

6,7,8,9,10,11,12,13,14

6,7,8,9,11,12,13,17,18,23,24,25,31,32,39,40,41,49,50,59,60,61

7,8,11,12,13,17,18,23,24,25,31,32

1,2,7,8

1,2,7,8,17,18,31,32,49,50

7,8,49,50

7,8

6,7,8,9,12

7,8,17,18,31,32,49,50

7,8,12

11,13,17,18,23,25

11,13,17,18,23,25,31,32

Table 1

Zernike modes included in each filter.
Examples of optical filters which may aid in detection of keratoconus.
This table does not list all possible filters – lists some of the better performing filters.

METHOD OF FILTERING DATA FOR THE OBJECTIVE CLASSIFICATION OF EYES

CROSS-REFERENCES TO RELATED APPLICATIONS

This application claims the priority benefit of U.S. Provisional Application Ser. No. 60/642,903, filed Jan. 11, 2005.

STATEMENT REGARDING FEDERALLY SPONSORED RESEARCH OR DEVELOPMENT

"The U.S. Government has a paid-up license in this invention, and the right in limited circumstances to require the patent owner to license others on reasonable terms as provided for by the terms of Contract/Grant No. EY R01 08520 awarded by the National Institutes of Health (NIH).

REFERENCE TO A "SEQUENTIAL LISTING"

Not Applicable

BACKGROUND OF THE INVENTION (1) Field of the Invention

The present invention relates generally to filtering optical measurement data for the determination of optical characteristics, and more specifically to filtering wavefront aberration data to detect and classify specific optical abnormalities of the eye.

(2) Description of the Related Art

The detection of abnormal optical properties of the eye provides the clinician with a powerful tool that can aid in disease detection, diagnosis, and patient management. Detection of corneal diseases is particularly important prior to laser surgery for refractive error because the inadvertent laser treatment of a diseased cornea can lead to serious post-surgical complications.

For example, keratoconus is a disease of the cornea contra-indicated for refractive surgery. The clinician typically identifies keratoconus from a corneal topograph by qualitatively assessing the asymmetry of the corneal shape as reflected typically by a dioptric curvature map of the cornea. Automated keratoconus detection schemas that quantify corneal asymmetry have been previously developed. These are ad hoc methods for extracting and quantifying the clinical observation of asymmetry from corneal topographic data. These methods are mostly platform-specific. Applying laser refractive surgery to a cornea with keratoconus or other abnormal condition(s) can lead to a complication called ectasia where the cornea stretches and distorts, with devastating consequences for vision.

Most corneal topographers available on the market today do not have any in-built optical defect detection schemas. Such topographers are used routinely as part of refractive surgery screening and, therefore, would benefit from the addition of such a schema. Similarly, wavefront sensors are entering into clinical usage, especially in refractive surgery. No known, commercially-available wavefront sensor has an optical disease detection schema, or abnormal optical defect detection schema.

Qualitative (by eye) reading of corneal topography is commonly used in a refractive surgery setting for screening for optical abnormalities. An automated quantitative index that is superior to the current ad hoc methods and easily adaptable to most corneal topographers and whole eye wavefront sensors is highly desirable because it is an objective method to support clinical interpretation and will assist in identifying abnormal optical states where surgery should be avoided. In a busy clinical setting such an automated objective detection system will help prevent cases of post refractive surgery ectasia and the resulting legal blindness.

BRIEF SUMMARY OF THE INVENTION

A method for classifying a patient's eye includes the steps of:

a. obtaining normal eye wavefront aberration data from a representative sample of normal eyes;

b. obtaining abnormal eye wavefront aberration data from a representative sample of a first class of abnormal eyes;

c. fitting the normal and abnormal eye wavefront aberration data with a basis function to decompose the normal and abnormal eye wavefront aberration data into normal and abnormal eye mathematical components;

d. examining the normal and abnormal eye mathematical components to develop mathematical optical filters capable of discriminating between normal and abnormal eyes, using statistical methods to define a probability distribution;

e. obtaining wavefront aberration data from the patient's eye;

f. fitting the patient's wavefront aberration data with a basis function to decompose the patient's wavefront aberration data into the patient's set of mathematical components;

g. examining the patient's set of mathematical components using the mathematical optical filters to generate a patient filter value; and h. classifying the patient's eye by comparing the patient filter value with the probability distribution.

In another feature of the invention, the step of examining the normal and abnormal eye mathematical components is done using receiver operating characteristics to generate an ROC value, and the step of classifying is done by comparing the patient filter value with the ROC value.

In another feature of the invention, the steps of obtaining wavefront aberration data are selected from the group of methods consisting of using a Shack-Hartmann wavefront sensor, using a ray-tracing wavefront sensor, and corneal topography. The corneal topography can be performed using various methods, including slit scanning corneal topography, stereographic corneal topography, placido corneal topography or any other instrument capable of reporting topographic data.

In another feature of the invention, the basis function is a Zernike expansion, but other basis functions deemed useful for development of optical filters can be used.

In another feature of the invention, the wavefront aberrations are obtained for only one ocular component of the eye, or a combination of ocular components of the eye.

In the present invention, data from an instrument that measures optical errors of the eye (e.g., the corneal first and/or second surface as measured by corneal topography, whole eye optical aberrations as measured by ocular wavefront sensors) is fit with a mathematical basis function to describe optical characteristics. The current standard mathematical description for describing the optical errors of the eye (Zernike expansion as described by ANSI Z80.28-2004) is used for the basis function. Filters to detect optical signatures are not limited to this particular basis function.

The Zernike expansion modes are used here to define an optical signature because the Zernike expansion is an ANSI standard basis function. Because certain Zernike modes (and/or combinations of modes) characteristically dominate the wavefront errors of eyes, the method of the present invention uses Zernike modes to identify that a given patient has the optical signature of a disease.

The method of the present invention includes platform independent optical "filters" (mathematical equations), based on Zernike modes, which aid in discriminating conditions of the eye from each other, and from normal eyes. The optical filters are used to describe the probability a given eye has a disease of the eye which affects its optical performance. In the embodiment described below, modes from the Zernike expansion are identified and a series of filters incorporating these modes are designed which discriminate between normal and keratoconus corneas. Although keratoconus is the abnormality described herein as an example of one embodiment of a set of optical filters to determine the probability an eye has keratoconus, the shape and optical signatures of other conditions (e.g., contact lens warpage, pellucid marginal degeneration, cataract development, surgical eyes, etc.) are also included in the scope of the invention.

BRIEF DESCRIPTION OF THE SEVERAL VIEWS OF THE DRAWINGS

Table 1 illustrates example optical filters (expressed in the form of a Zernike expansion) for the detection of keratoconus. This table is not exhaustive and is provided to illustrate the principle of an optical detection filter.

DETAILED DESCRIPTION OF THE INVENTION

Figure 1:
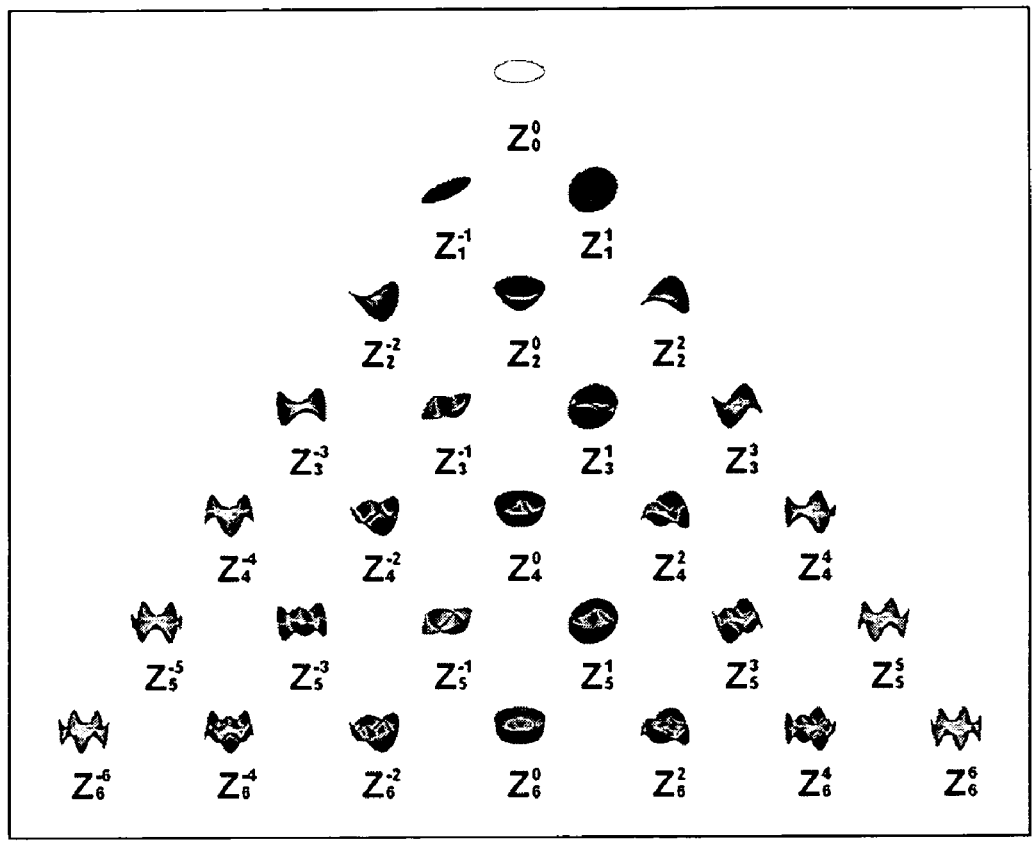
FIG. 1 displays a subset of the modes (shapes) of the Zernike expansion. A Zernike expansion is just one of the many basis functions that can be used to build filters for the detection of optical signatures of interest.

The present invention describes the use of a basis function decomposition of the corneal and/or eye's wavefront aberration data to define optical signatures of a variety of abnormal eye conditions. These signatures are used to aid in differentiating normal from abnormal eyes by defining optical filters capable of detecting and differentiating each type of optical signature and the probability that the given set of optical signatures are consistent with the optical signatures of the eyes having a particular disease or set of diseases. Such a fit defines the optical defects in terms of a series of mathematical components (unique shapes of optical error), with each mathematical component being weighted by its contribution to define the optical signature.

To simplify the description of the present invention, the following describes the technique of the present invention as it pertains to the keratoconus eye. The particular filters used to differentiate the normal eye from the keratoconus eye are based on the Zernike polynomial decomposition of wavefront aberration data but can also be based on any one of many different basis functions (e.g., Taylor series, Fourier series, etc.) besides the Zernike polynomial. The approach is equally applicable to wavefront aberration data measured on a wavefront sensor, wavefront aberration data calculated from corneal shape data captured with a corneal topographer, or in combination.

The Zernike polynomial expansion is described fully by the ANSI standard ANSI Z80.28-2004. Briefly, the Zernike polynomial consists of three terms. The first term is a normalization term, the second is a radial term, and the third is a meridional term. The general form for the Zernike polynomial expansion is given by:

$$Z_n^m = \begin{cases} \sqrt{2(n+1)}\, R_n^{|m|}(\rho) \cos(m\theta), & \text{for } m > 0 \\ \sqrt{2(n+1)}\, R_n^{|m|}(\rho) \sin(|m|\theta), & \text{for } m < 0 \\ \sqrt{(n+1)}\, R_n^{|m|}(\rho), & \text{for } m = 0 \end{cases}$$

and $$R_n^{|m|}(\rho) = \sum_{s=0}^{0.5(n-|m|)} \frac{(-1)^s (n-s)!}{s!\,(0.5(n+|m|)-s)!\,(0.5(n-|m|)-s)!} \rho^{n-2s}$$

where:
  n: radial order index for Zernike functions (non-negative radial integer index)
  m: meridional index for Zernike functions (signed meridional index)
  ρ: radial parameter for Zernike functions (real number continuous over its range of 0 to 1)
  θ: meridional parameter for Zernike functions (real number continuous over its range of 0 to $2\pi$)

A surface estimate can be described by the Zernike polynomial as follows:

$$S(\rho, \theta) = \sum_{all\ n\ and\ m} c_n^m Z_n^m$$

where:
  $c_n^m$: Zernike coefficient

The modes are defined by their angular frequency (m) and radial order (n) and can be visualized in a periodic table (FIG. 1). The description of Zernike modes as $Z_n^{\pm m}$ defined immediately above is known as double index notation. Another common method for referring to Zernike modes is a single index notation, where Zernike modes are numbered from 0 to n, starting with the mode on the top of the Zernike pyramid and working down in a left to right order. Certain modes tend to occur in certain conditions, or as a result of surgery. While many aberrations exist in keratoconus, coma ($Z_3^1$, $Z_3^{-1}$ in double index notation or Z7 & Z8 in single index notation) tends to be the dominant higher order mode.

Individual aberration modes, paired modes, and combinations of modes have been iteratively considered for their ability to discriminate between normal and keratoconus subjects using Receiver Operating Characteristic (ROC) analysis. A series of filters which use combinations (by root mean square—RMS) of Zernike modes to accurately discriminate between normals and keratoconus have been identified. This was done by looking at the ability of each Zernike mode, and combinations of modes to discriminate between normals and keratoconus cases. The more discriminating modes were combined by squaring the coefficient of each mode, adding and then taking the square root of the sum ($\sqrt{(c_a^2 + c_b^2 \ldots)}$) since modes can have negative sign (commonly referred to as RMS error). This process continued logically and iteratively until a series of best discriminating combinations was identified. To illustrate, a number of particularly useful filters for identifying keratoconus are listed in Table 1. Similar procedures could be used to identify and differentiate other optical conditions of interest (including normal) using a number of different basis functions.

In summary, the method of the present invention, which is a method of classifying a patient's eye, includes the following steps:

| STEP | Description |
|------|-------------|
| 1 | Obtaining a first and a second set of wavefront aberrations of the whole eye or a component by any of a number of means (e.g. Shack-Hartmann Wavefront Sensor, Ray tracing Wavefront Sensor, Corneal Topographer, et cetera) corresponding to two groups of clinically diagnosed eyes (e.g., keratoconus and normal, any optical disease and normal, two optical diseases of the eye, combinations of optical diseases and normal. The other-than-normal eye, or "abnormal" eye, can also include a healthy eye that has been altered, such as surgical eyes or eyes with optical appliances, or other conditions that filters would be good for, where the eye is not diseased but is altered by some other cause.). |
| 2 | Fitting the two groups of measured wavefront aberration data with a basis function (here we use an illustrative example of a useful basis function the Zernike expansion, but any of a number of other basis functions could be used) to decompose the wavefront data into normal and abnormal eye mathematical components. |
| 3 | Examining the normal and abnormal eye mathematical components to develop mathematical optical filters capable of discriminating between normal and abnormal eyes, using statistical methods (using Receiver Operating Characteristic analysis in the preferred embodiment, but other methods can be used) to define a probability distribution |
| 4 | Obtaining wavefront aberration data from the patient's eye |
| 5 | Fitting the patient's wavefront aberration data with a basis function to decompose the patient's wavefront aberration data into the patient's set of mathematical components |
| 6 | Examining the patient's set of mathematical components using the mathematical optical filters to generate a patient filter value; and |
| 7 | Classifying the patient's eye by comparing the patient filter value with the probability distribution |

The best optical filters have the highest ability to discriminate between the two groups under test. The approach of using wavefront aberrations to identify abnormal characteristics also is applicable to the detection of other ophthalmic conditions or surgical states. For instance, the detection of previous refractive surgery is desired by armed forces admissions agencies. Similarly, the probability that a patient has one or a combination of any other optical conditions or states may be determined by defining its optical signature or "fingerprint", and the optical signature can then be used to aid in differentiating this patient from normal. Optical filters could be developed for example to aid in detecting cataract, lenticonus, microspherophakia, keratoglobus, pellucid marginal degeneration, Terrien's marginal degeneration and pterygium. It can also be used to aid in detecting the effects of surgery and prostheses, corneal transplantation, contact lens induced corneal warpage and optical appliances such as contact lens and IOLs. The use of basis functions facilitates the ease at which optical signatures are defined and are platform independent—i.e. the filter defining the optical condition does not depend on the operating characteristics of the particular measurement system. Instead, the filter depends on the ability of the machine to make an accurate measurement and the ability of the operator to use the instrument properly.

While this invention has been described fully and completely and demonstrates the value of optical detection filters by concentrating on the detection of keratoconus, it should be understood that, within the scope of the appended claims, the invention also incorporates detection filters for other optical abnormalities. Although the invention has been disclosed with reference to its preferred embodiment, from reading this description those of skill in the art can appreciate changes and modifications that may be made which do not depart from the scope and spirit of the invention as described above and claimed hereafter.

What is claimed is:

1. A method for classifying a patient's eye, comprising the steps of:
   a. obtaining normal eye wavefront aberration data from a representative sample of normal eyes;
   b. obtaining abnormal eye wavefront aberration data from a representative sample of a first class of abnormal eyes;
   c. fitting the normal and abnormal eye wavefront aberration data with a basis function to decompose the normal and abnormal eye wavefront aberration data into normal and abnormal eye mathematical components;
   d. examining the normal and abnormal eye mathematical components to develop mathematical optical filters capable of discriminating between normal and abnormal eyes, using statistical methods to define a probability distribution;
   e. obtaining wavefront aberration data from the patient's eye;
   f. fitting the patient's wavefront aberration data with a basis function to decompose the patient's wavefront aberration data into the patient's set of mathematical components;
   g. examining the patient's set of mathematical components using the mathematical optical filters to generate a patient filter value; and
   h. classifying the patient's eye by comparing the patient filter value with the probability distribution.

2. The method of claim 1, wherein the step of examining is done using receiver operating characteristic analysis in the statistical methods.

3. The method of claim 1, wherein the steps of obtaining wavefront aberration data are selected from the group of methods consisting of using Shack-Hartmann wavefront sensing, ray-tracing, corneal topography, and any method capable of producing wavefront aberration data.

4. The method of claim 1, wherein the basis function is selected from a group consisting of a Zernike expansion, Taylor series, Fourier series, and any basis function useful in development of optical filters.

5. The method of claim 1, wherein the wavefront aberration data are obtained for only one ocular component of the eye.

6. The method of claim 1, wherein the abnormal eyes comprise eyes having abnormalities comprising Keratoconus, Cataract, Lenticonus, Microspherophakia, Keratoglobus, Pellucid Marginal Degeneration, Terrien's Marginal Degeneration, Pterygium, and refractive error.

7. The method of claim 1, wherein the first class of abnormal eyes are eyes that are using an optical appliance.

8. The method of claim 7, wherein the optical appliance is taken from the group consisting of contact lenses and intra-ocular lenses.

9. The method of claim 1, wherein the first class of abnormal eyes are eyes that have had a change in optical properties resulting from the use of an optical appliance.

10. The method of claim 1, wherein the first class of abnormal eyes are eyes that have had a change in optical properties resulting from surgery.

11. The method of claim 1, wherein the normal eyes are a second class of abnormal eyes.

12. The method of claim 3, wherein the corneal topography is performed using a method selected from the group consisting of slit scanning corneal topography, stereographic corneal topography, and any instrument capable of reporting topographic data.

13. The method of claim 1, wherein the wavefront aberration data are obtained for several ocular components of the eye.

* * * * *